United States Patent [19]
Thind

[11] Patent Number: 5,737,870
[45] Date of Patent: Apr. 14, 1998

[54] BAIT AND TRAP

[75] Inventor: Bharat B. Thind, Cranford, Great Britain

[73] Assignee: The Minister of Agriculture Fisheries and Food in her Britannic Majesty's Government of the U.K. of Gt. Britain & N. Ireland, United Kingdom

[21] Appl. No.: 537,692
[22] PCT Filed: Apr. 29, 1994
[86] PCT No.: PCT/GB94/00916
  § 371 Date: Nov. 3, 1995
  § 102(e) Date: Nov. 3, 1995
[87] PCT Pub. No.: WO94/24859
  PCT Pub. Date: Nov. 10, 1994

[30] Foreign Application Priority Data

Apr. 29, 1993 [GB] United Kingdom ............... 9308868

[51] Int. Cl.⁶ ........................................... A01M 1/20
[52] U.S. Cl. ........................ 43/107; 43/114; 43/121; 43/132.1
[58] Field of Search ............................... 43/114, 132.1, 43/131, 107, 121

[56] References Cited

U.S. PATENT DOCUMENTS

| | | |
|---|---|---|
| 4,218,842 | 8/1980 | Anderson . |
| 4,520,015 | 5/1985 | Pesche . |
| 4,930,251 | 6/1990 | Crisanti . |
| 5,009,710 | 4/1991 | Bewsey ............... 43/132.1 |
| 5,172,514 | 12/1992 | Weber ................ 43/132.1 |
| 5,238,681 | 8/1993 | Chang ................ 43/132.1 |
| 5,396,729 | 3/1995 | Vejvoda ............... 43/114 |

FOREIGN PATENT DOCUMENTS 800736  9/1958  United Kingdom .

OTHER PUBLICATIONS

WPI Abstract Accession No. 78-35942 A/20 & JP53/038594 (Lacton Kagaku Kogyo) Fishing Bait.

*Primary Examiner*—Kurt Rowan
*Attorney, Agent, or Firm*—Nixon & Vanderhye

[57] ABSTRACT

A bait is provided particularly adapted for attracting and arresting mites such that when used in a particular trap it allows non-destructive collection of mites from a produce. This enables study and enumeration of mites to be more easily carried out than with previous bait/trap combinations. The bait takes the form of an aqueous gel body which is then mounted within an apertured container which forms the trap. The gel may further contain other attractant and arrestant components and its use allows mechanical trapping mechanisms to be dispensed with.

A method of assessing infestation status and a trap for mounting the bait are also provided, together with methods for using the bait and/or trap as a microbial detector.

25 Claims, 3 Drawing Sheets

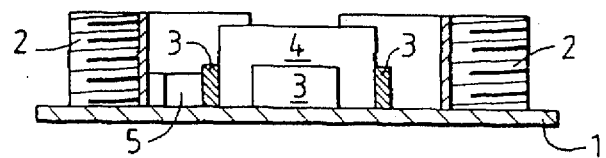
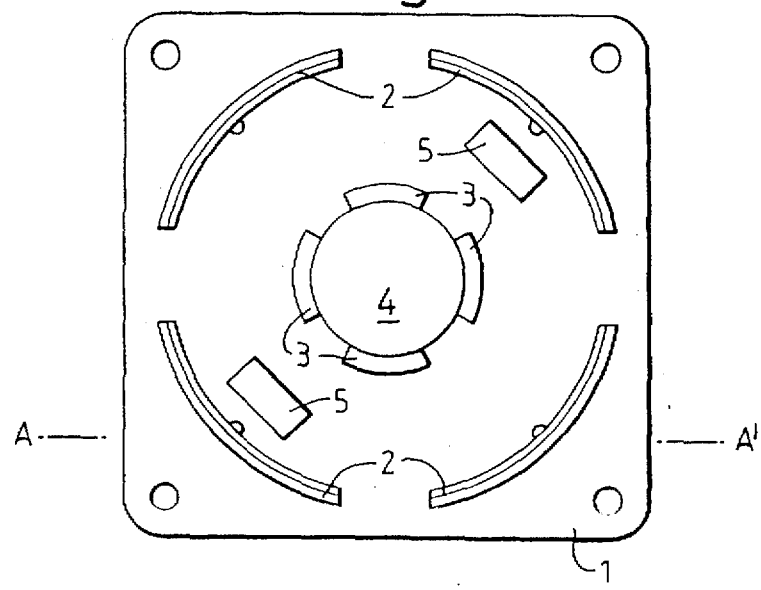
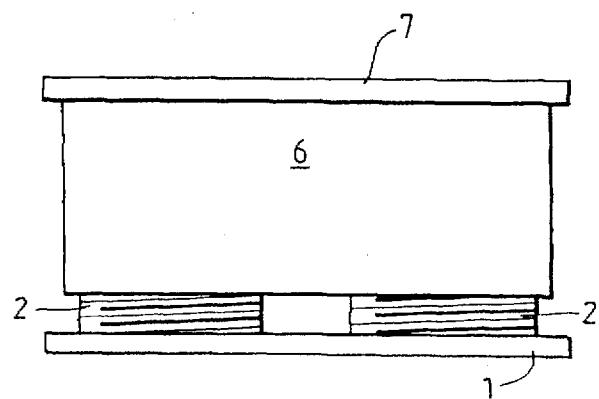

MOISTURE LOSS OF STANDARD BAIT FORMULATION AT VARYING TEMPERATURES AND HUMIDITIES.

A COMPARISON OF MITES ATTRACTED BY BT TRAP BAIT AND CARRAGEENAN BAIT HOUSED IN IDENTICAL CONTAINERS.

BAIT AND TRAP

The present invention relates to bait suitable for attracting and/or arresting insect and/or arachnid pest animals, particularly storage pests such as mites, and further relates to a trap for mounting such bait in use. Also provided is a method for use of the bait and trap for pest control and/or assessment of infestation status of stored produce and premises dealing with storage, production and distribution of such produce. Preferred traps include microbial indicators capable of detecting specific microorganism associated with the pest animals.

Various environments are subject of infestation by insect and arachnid pest animals such as cockroaches, beetles and mites; particularly environments such as stored consumable produce, such as grains, and premises dealing with storage, production and/or distribution of these. It is known to use baits to trap these pests.

A first known type of pest bait currently in use is a mixture of cereal, peanut and carobs deployed in the form of bait bags consisting of rectangular perforated plastic bags containing the mixture. These bags are used for trapping a wide variety of insect pests but may be used to trap mites by virtue of the attractant power of the high moisture content carobs. However, the bags are not specifically designed for the task and enumeration of trapped mites is slow and inefficient; separation from the bags involving shaking them over a container. This process, although well suited for isolation of insects, is inefficient and extremely destructive for mites, and thus prevents their further study once isolated.

In dusty production and distribution areas the effectiveness of bait bags is diminished due to their large apertures which allow a considerable quantity of fine powdery debris to settle inside them. Isolation of mites from debris contaminated bags is inefficient and labour intensive.

A second known type of bait in use is fish meal and is deployed in the form of a moistened filter paper having the meal placed at its centre. The paper is covered with a petri-dish raised from its surface by a few millimeters, eg. using paper clips. In this trap moisture plays an important Pole in attracting the mites and thus attractancy is short lived due to the absence of a moisture regulating mechanism. In addition such traps are easily disturbed and it is difficult to set and retrieve them from confined spaces. Again, the procedure for detecting and isolating mites from such traps is labour intensive and requires experienced personnel.

It is known to trap insects using carrageenan gel baits wherein carrageenan is used as both gelling agent and insect attractant which leads to the bait being ingested (see WO 91/07972). In this bait the carrageenan is used with quantities of 25% or 98% water by weight for attracting cockroaches and 50% water by weight for ants; in each case the bait is insecticidal and the attracted insects are killed on its ingestion. The trap or bait are not shown to work with mites and, indeed, carrageenan is found not to be an attractant for mites by the present inventor and they are not suited to suspension in produce.

It is known to use live nematodes as bait fop killing insects whereby live infective juvenile nematodes are supported in a gel impregnated into a reticulated foam with a 1 to 5 mm region at its top being in the form of a high surface area which must be dry to encourage nictation (see WO 92/08356); carrageenan or agar set with hygroscopic salts are used as nematode slow release support gels. This document notes that cockroaches are attracted to moist closed spaces and provides this using liquid water supplied through a water permeable membrane or from a separate water liberating swelled polyacrylamide gel to that which acts as support to the nematodes. Suspension in product is not disclosed.

Other bait and pesticidal compositions of gelled nature are known. Fishing baits are known made from tamarind gum, egg yolk, shrimp mince. D-sorbit and agar with about 33% by weight water content.

It is known to apply fungi in agar gel to manure for the purpose of destroying eelworm nematodes therein (see GB 800,736); in this case the agar gel merely serves as a carrier and not a bait. It is further known to use alginate gels as carriers for pesticidal mollusc and mammal baits wherein toxic materials are incorporated with foodstuffs within a gel matrix (see U.S. Pat. No. 4,520,015). All these known baits have as their aim the destruction of the target animal.

There is a clear need for a bait and trap and their combination that can attract and retain insects or arachnid pest animals, particularly mites, can detect them in low numbers, this facilitating isolation and examination, is relatively stable, can easily be placed and retrieved and can be used in a variety of situations; particularly being more sensitive than known mite traps. There is a further need for a robust bait and trap that can indicate presence of pathogenic microorganisms present in association with pests in a rapid, easy to use manner.

The present inventor has now provided a method for assessing the infestation status of an environment subject to infestation by insect and/or arachnid pest animals, particularly mites, together with a novel bait suitable for use in insect and arachnid pest animal traps, particularly mite traps, and a novel trap containing such bait whereby at least some of the aforesaid needs are addressed.

According to a first aspect of the present invention there is provided a method for assessing the infestation status of an environment with respect to insects and/or arachnid pest animals comprising placing a trap in the environment that is capable attracting the pest animals and arresting them therein; maintaining the trap in the environment for a predetermined time sufficient to attract a representative amount of the pest animal population; thereafter removing the trap and relating the number and/or type of animal arrested therein to the infestation status of the environment: characterised in that the trap includes a non-harmful non-flowing aqueous gel body having water content sufficient to act as an arrestant for the pest animals. Preferably the water content is from 65 to 98% by weight, more preferably 70 to 87% by weight, most preferably about 75% by weight.

Preferably the gel bait used is such that insects and/or arachnid pest animals are able to survive on it in a living state for the predetermined time, and preferably after the predetermined time the insects and/or arachnids on the bait are enumerated, identified and/or further characterised.

In a most preferred form of the invention the trap includes a microbial detector capable of detecting the presence of one or more types of microorganism associated with the insects and/or arachnid pest animals. Preferably this detector comprises a microbial growth medium and preferably one that undergoes a colour change when microbes grow in or in it. Such microbial growth medium may be provided as the aqueous gel body itself or further a such body, optionally lacking all the attractant/arrestants of the bait gel body, included in the trap. The method of the present application has particular application in the assessment of infestation with mites such that, inter alia, their numbers, type (eg. species), pesticide susceptibility and the nature of microorganism species associated with them may be determined.

Preferred time for leaving the traps in the environment is from 1 to 10 days; after such time the bait will be likely to have dehydrated to the point of offering minimal pest supporting arrestant properties (see FIG. 3); more preferably this time is from 4 to 7 days.

The environments where the present method has particular application are stored produce or premises dealing with storage, production and/or distribution of produce. Such produce may for example be any foodstuff that is susceptible to infestation with insect or arachnid storage pests; eg. bulk storage produce such as grains and cereal based foods, but in principle any consumable produce and the place where that is stored and/or processed may be assessed by the method.

A further aspect of the present invention provides use of a bait comprising a non-toxic non-flowing aqueous gel body formed from a mixture of an aqueous component and one or more further gel forming components, wherein the water content of the bait is sufficient for the purpose of acting as arrestant for the insect or arachnid pest animals; these preferably being mites. Preferably the water content of the gel is 65 to 98% by weight. Agar and/or an alginate are preferred further gel forming components. For some gelling agents, eg. carrageenan, water content such as 98% still allows a non-flowing body to be produced. Preferably the bait body water content is from 70 to 87% by weight, most preferably about 75% by weight. Such content provides maximal arresting of pests while allowing the body to be hard enough to maintain shape, ie. not to flow from its mounting when placed on a surface which may be at an angle to the horizontal, yet does not render it too brittle to be impaled. In this manner the bait is suitable for placement in a trap that is suspended from a cord in particulate produce or which is affixed to a wall of a vessel or other container. Furthermore carrageenan bodies are too incoherent at high water levels to prevent their breaking up when the bait and traps are washed for the purposes of removing pests for further studies.

In order to maximise the attractancy of the bait for the pest animals it will be advantageous to incorporate attractant and/or other arrestant agents which act in addition to the water content into the gel body. Preferably the bait includes agents in addition to the water that help to arrest the pest animals, such as agents providing a suitable diet for ensuring that pest is maintained alive for the predetermined period. Obviously where the bait is positioned in a food produce it is not necessary to incorporate foods other than water to keep the pests alive, however it is desirable to include these to keep the pests content in the trap. Suitable attractants/arrestants for mites include fishmeal, wheatgerm, wheatgerm oil, yeast, fish oil, liver (eg. ground liver), pectone, glucose, glycerol and pheromones. Other pests such as ants and cockroaches may respond to other foods.

In a further aspect of the invention there is provided a non-harmful bait suitable for the purpose of attracting and/or arresting insect and/or arachnid pest animals comprising a non-flowable aqueous gel body formed from a mixture of an aqueous component and one or more further gel forming components; the bait comprising a water content sufficient to act as arrestant for the pest animal. Preferred water content is from 65 to 98% by weight, and for agar gels is preferably 70-87% weight, more preferably about 75% weight, in order to provide the required stability and allow mounting by impaling bait upon one or more projections of a trap.

Preferably the bait further comprises one or more microbial detector components, these preferably comprising a microbial growth medium, preferably one that undergos a colour change when general or specific microbes are grown on it.

In a still further aspect of the present invention there is provided a trap, suitable for attracting and/or arresting insect and/or arachnid pest animals, particularly mites, comprising a housing having an interior surface including a mounting means for immobilising a non-flowing gel bait against movement when the trap is inverted, and one or more access openings for admitting entry of the insect and/or arachnid pest animals: the mounting means comprising one or more projections on or between which the bait is secured in use such that the bait has at least one surface exposed within the housing.

Preferably the housing has a lid portion and and a base portion with the mounting means provided on an interior surface of at least one of the lid and the base, the base preferably being configured to allow stable placement upon a flat surface or the trap having fixing means allowing its stable placement placement on angled or vertical surfaces. Preferably the fixing means is an adhesive pad, or a cord on which the trap may be suspended. It is a unique feature of the bait and trap of the invention that they can be suspended or mounted at any angle to the vertical and retain the ability to attract and arrest target pests over a period of days while allowing ready separation of bait and for pests for examination purposes. Particularly the bait and trap allow suspension by means of cords such that the bait rests within a food produce such as a grain and can be retrieved by pulling the cord to remove the trap or bait from the produce.

Preferably one or both of the lid and base, or a further portion with which these engage, has gaps in the sidewall the size of which is determined by how closely the portions engage. In this manner the rate of moisture loss of the bait can be controlled dependent upon the humidity of the environment in which the trap is placed. Preferably the trap has polygonal surfaces on the lid and/or base and/or projections from the housing wall or walls which prevent it from rolling displacement.

Again, preferred traps of the present invention include a solid aqueous gel bait and/or solid gel microbial detector bodies immobilised on the mounting means. Such traps thus may be used as microbial detector devices. Preferred microbial detector devices are targeted at pathogenic organisms associated with food poisoning, such as Salmonella and/or Listeria microorganisms. Growth media which undergo colour change when these specific microorganisms grow in or on them are commercially available eg. as described in the Examples.

Use of the non-harmful, non-flowing gel body bait of the present invention is particularly suited to studying mite infestation as it allows attraction and retention without the need to mechanically trap them, thus good access to the bait may be provided which allows ease of separation of mites after use.

This freedom not to mechanically trap the target pest, yet not to kill it, allows use of very simple trap housings. One such simplified housing comprises a conduit with two open ends,.the conduit conveniently being a rectangular section plastics conduit having an inner volume with a cross section of about 1.5×1.5 cm and a length of about 5 cm. Within the inner volume are provided one or more projections extending outward from one of its surfaces such that a gel bait of a few mm thickness and 1 or 2 cm long may be inserted and impaled upon them to be retained thereon even when the trap is dislodged or held at an angle. The trap is then placed on a flat surface, or is suspended in a produce by a cord affixed through one of its surfaces and allowed to attract and retain pest animals, particularly being designed for mites.

A particular application of the bait and trap of the present invention is in assessing presence of microorganisms carried by pests, such as salmonella and listeria. By incorporation of microbial indicators into a growth support medium the presence of these potentially harmful bacteria may be indicated; many such indicator media being provided as dry components which can be substituted for the gel former in the bait and a gel body formed. Preferably the indicator is formed into a gel and placed in the trap separate from the main bait.

Using bait for such purpose makes sterilisation of the trap desirable where reuse is envisaged. For this purpose the trap housing should preferably be made of a heat stable plastics,.and for reuse in general is preferably a strong plastics such as nylon preferably reinforced with fibrous material such as glass fibre; this allowing machining of fixing holes, autoclaving and providing resilience.

It will further be realised that the trap may include other portions as well as the lid and base. Such portion or portions might readily be provided without affecting operation of the trap. Whatever the arrangement, it is preferred that the trap allows air flow through the trap to be controlled and thus the rate of water loss can be set to suit the environment in which the trap is being used. Any threaded engagement should be sized and made of such material that they will not move relative to each other when the trap is moved as a whole. It will further be advantageous that the trap includes or is made of a distinctively coloured material for highlighting its position in use such that it seen easily for retrieval from produce.

Microbial detectors used may be the preferred colour changing gels as described above, or may take the form of an adsorbent body impregnated with antibodies to the target organism in the gel; thus a positive detection would provide a clear area in the gel around the bait.

The method, bait, trap and detectors of the present invention will now be illustrated by way of example only by reference to the following non-limiting examples of bait and traps of the invention and the accompanying Figures. Further embodiments falling within the scope of the claims will occur to those skilled in the art in the light of these.

FIGURES

FIG. 1 shows a cross section through a base of a trap of the present invention showing the interior and particularly the bait mounting.

FIG. 2 shows a plan of the base of the trap of FIG. 1, the line A-A' being that through which the cross section of Figure is taken in a direction from bottom to top of the Figure.

FIG. 3 shows an elevation of an assembled trap according to the invention.

EXAMPLES

Example 1

Figure 4:
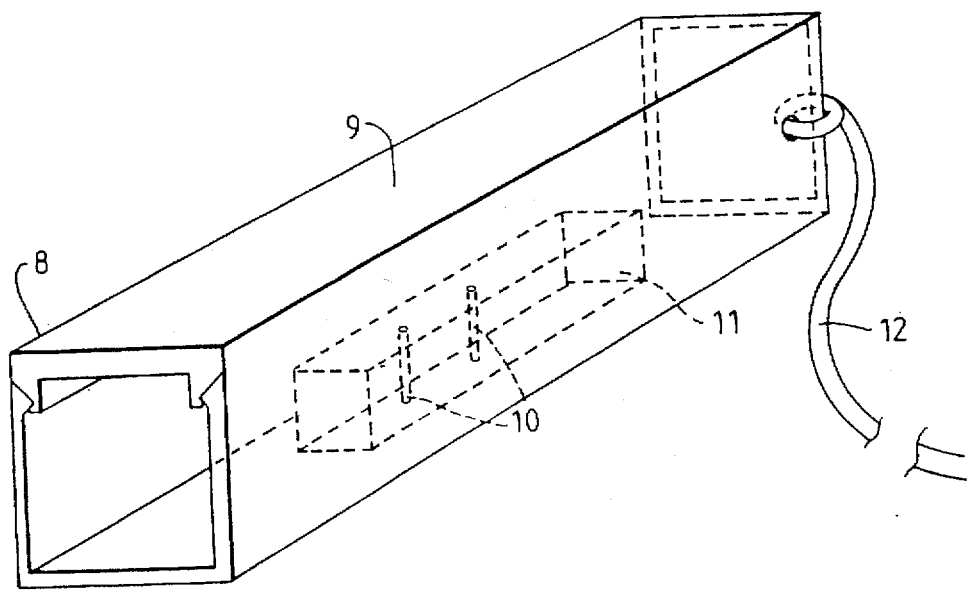
FIG. 4 shows a simple rectangular cross-sectioned trap of the invention.

A bait mix for use in 60 traps of the present invention was made by preparing an agar gel by standard procedures using the following components:

33.3 g fishmeal; 13.3 g pectone (Unipath Ltd); 10 g debitted Feast; 3.3 g wheat germ; 11.67 g Agar Technical (Unipath Ltd: Agar No.3); 50 ml glycerol (Mar & Baker Ltd); 12.5 ml cod liver oil (Lloyds Health foods); 500 ml distilled water.

All apparatus was sterilised before use. The fishmeal, wheatgerm and yeast were autoclaved before use at 121° C. and 1 atmosphere for 20 minutes, the cold distilled water placed in a 1 liter flask and the agar added and stirred in until a suspension was formed in the water. The flask was heated without boiling on a hotplate until the agar dissolved and a clear solution formed. The flask was removed from the heat and the peptone added slowly while simultaneously stirring to allow even dispersion.

Stirring was continued while adding the wheatgerm, yeast, fishmeal, glycerol and cod liver oil. The mixture was then allowed to cool to around 60° C. before pouring into square petri dishes to a depth of 1 cm, making sure that the contents of the flask are constantly agitated in order to maintain an even dispersal of the constituents. The petri dish was then covered and left to cool further. On solidification the bait was cut to the desired size to fit traps using a sterile scalpel.

Example 2

A trap according to the present invention was provided by use of lid and base components as illustrated in FIGS. 1 to 3 in which a bait according to Example 1 was placed and the two components assembled by screwing them together such as to provide a desired cross-section of through hole to control water loss in a given environment.

FIG. 1 is a cross section of the base of FIG. 2 as taken through line A-A' looking from the bottom to the top of the page. The trap base (1) mounts integral wall elements (2) extending perpendicularly to it. These elements bear screw threads on their exterior surfaces that are aligned such that they engage the interior walls extending from the top of a lid section in use by screw fit.

Gripping elements (3) extend perpendicularly from base (1) to a distance less than the height of its walls (2) and define a space between them such that a standard size of gel bait (4) of the invention may push fit between them, optionally further being retained on a spike element in the centre of the base within the defined space. In addition to the bait (a gel block of about 2 cm×2 cm×1 cm), microbial indicator gel blocks (5), comprising gels made solely from the solid media described in Example 4, are impaled upon projections from the base at oppositely positioned points within the trap. These indicators may be of similar function, eg. for detecting for salmonella, or may detect other types, eg. listeria.

FIG. 3 shows an elevation of the assembled trap, wherein a lid (7) with internally threaded depending sidewall (6) has been screwed down over the base leaving apertures for entry of mites. These are of the order of several millimeters high, the lid itself being of about 7.5 cm across and about 1.6 cm high. Thus the apertures are not sized to prevent exit of mites, but reliance is placed upon the retentive effect of the bait.

The base was placed on a flat surface and the bait placed at its centre over the central spindle and impaled upon that, pushed down, until it rests on the base of the trap.

Any further detection agents were then placed within the base structure of the trap onto the projections, eg.spindles, provided and pushed down to be restrained by resting against the base. The lid of the trap was then placed over the base section and screwed down until an aperture of around 5 mm height was provided. The trap was then ready for lifting and placement.

Example 3

The trap as described in Example 2 was placed in a variety of locations including production premise floors, and in raw finished products, with the screw fit of base and lid set to provide apertures of dimension 0.25 to 1 cm$^2$ and left for a period of between 4 and 7 days. At the end of this period the lid and base were separated and the contents of the trap removed by the process described below.

Filter paper (Whatman No 41: 12.5 cm diameter) was placed on a 3 piece Hartley funnel, dampened with distilled water, a connected vacuum pump activated and the funnel collar placed onto the filter paper. The two halves of the trap were separated and the internal surfaces washed with distilled water over the collar. The bait was held in forceps, washed thoroughly with distilled water making sure that that was all caught within the collar. The pump was switched off and methylene blue dye applied to the paper within the confines of the collar until it is evenly dyed; the pests do not stain. The vacuum pump was switched on to remove excess liquid and then off for paper removal. The paper was then placed in a large petri dish and examined under the microscope for presence of and type of mites. Mites so isolated were kept for further study and breeding if prolonged studies were necessary.

Example 4

The bait preparation of Example 1 was carried out using a listeria selective agar base (Oxoid Formulation CM 856 with listeria selective supplement SR140) based upon the formulation of Curtis et al (1989) Monocytogenes, Letters in Applied Microbiology 8 95–98, in pace of the agar component. Presence of listeria produces black zones around the colonies. XLD medium was substituted for the agar for the detection of salmonella. Both these agars and their associated tests and that using Brain Heart Infusion agar for general microorganisms are described in 'The Oxoid Manual of Culture Media, Ingredients and other Laboratory Services' Fifth Edition, 1982 and 'Selective Microbiology for Food and Dairy Laboratories' March 1990, Folio No. 169. Reprint February 1991. Traps baited with these agars, or with indicator gel blocks in addition to a gel bait, were used as described in Example 3. For general detection gels made from a support medium such as Brain Heart Infusion Agar may be used and microbes present determined on bait removal, or this may include antibodies to specific microbes on bodies in the detector gel whereby clear areas around a body impregnated with specific antibody indicates presence of the specific microbe.

Example 5

A simplified trap of the invention was provided as shown in FIG. 4 using a conduit of rectangular section (8) with one wall (9) that is disengagable from the others such as to expose the interior thereof. A pair of projections (10) are provided in the centre one of the other walls extending toward the interior of the assembled conduit. For use a bait of the invention (11) is impaled upon the projections and the wall (9) replaced. A cord (12) is optionally provided passing through one of the other walls and is used to retrieve the trap from a foodstuff in which it is placed for performance of the method of the invention.

Example 6

Figure 5:
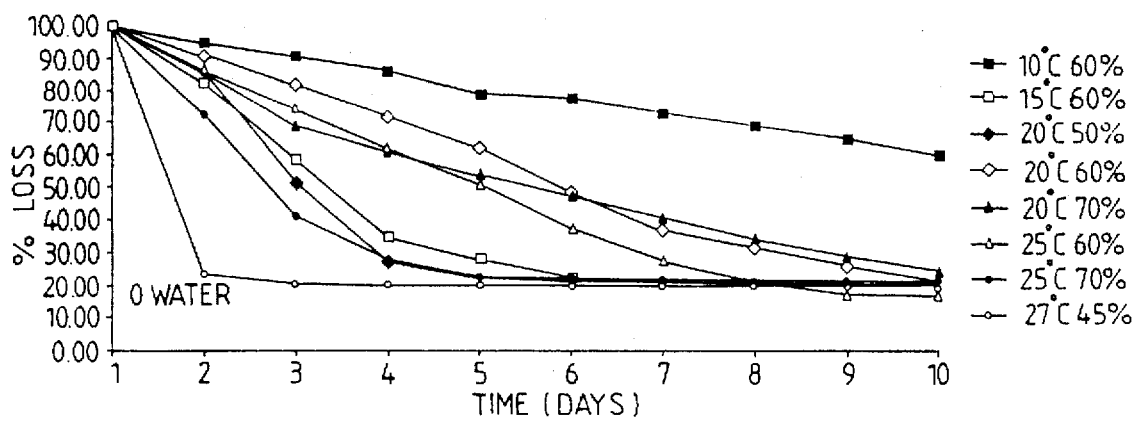
FIG. 5 shows the rate of loss of water from gel baits over a 10 day period under different humidity conditions.
Figure 6:
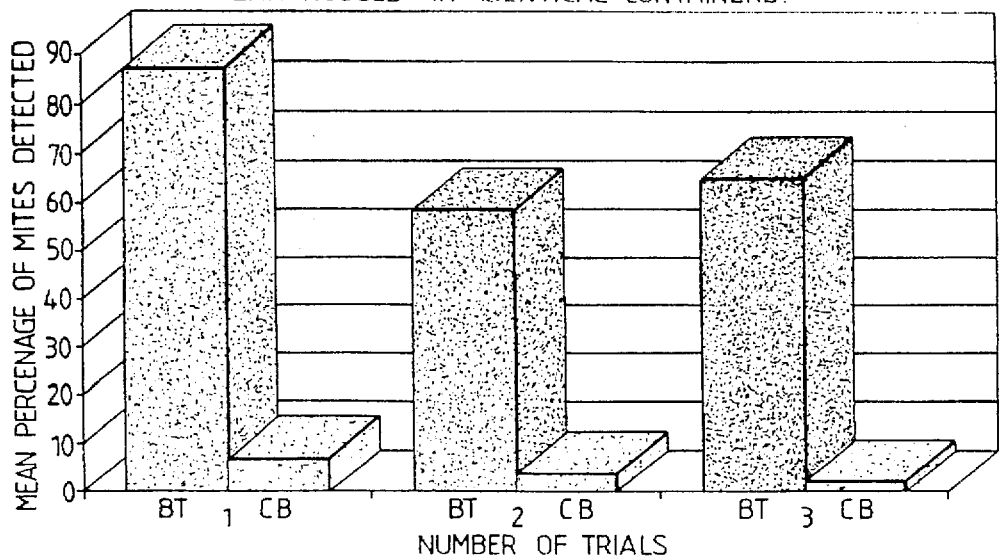
FIG. 6 shows a histogram comparing the number of mites arrested by agar traps of the present invention, Example 1, as compared to carrageenan bait (of WO 91/07972) lacking its toxic component.

The useful life of the baits of Example 1 when placed in a variety of temperatures and humidities is shown in FIG. 5.

It can be seen that for 27° C. and 45% humidity the trap of Example 2 would need to be set with the pest entry apertures as small as possible while allowing entry of mites and/or by use of increased water content bait. It will also be possible that in low humidity environments some pest at least will be sampleable in a shortened period of time due to the lack of other water sources.

Example 7

The relative efficacies of agar based gels and carrageenan based gels in attracting mites was investigated using traps as described in Example 5 each baited with one of these bait gels and placed within a secure but aerated container of 18 inches diameter across its bottom. The container is loaded with a population of mites and the interior maintained in a state of darkness, as would be expected in storage.

Table 1 illustrates the results of competitive attraction and arresting capability tests wherein each type of bait is competed against another by placing it in three traps and the other bait in three traps, arranging the traps in a circle around the bottom of the container and examining them after 24 hours. Such period is not typical of that used in an infestation status assessment but suffices for assessing relative attractancy. A number of mites are placed in the centre of the container; the number varying with each test. Baits are: BT—Agar bait of Example 1, CB—Carrageenan 2%/water 98%, CF—As Example 1 but with carrageenan provided in place of agar.

TABLE 1

| Bait type A | Mites arrested | Bait type B | Mites arrested |
| --- | --- | --- | --- |
| BT | 499 | CB | 68 |
| BT | 317 | CF | 122 |
| BT | 607 | CF | 200 |

I claim:

1. A method for assessing the infestation status of an environment with respect to insects and/or arachnid pest animals comprising the steps of:
   (1) placing in the environment a trap which is capable of attracting the pest animals and detaining them therein the trap comprising a housing containing a non-flowing aqueous gel bait which is non-harmful to the pest animals, said housing having adjustable openings to allow access of pest animals and to control the rate of evaporation from the bait, the water content of the bait being sufficient to ensure that the pest animals are detained within the housing;
   (2) maintaining the trap in the environment for a predetermined time sufficient to attract a representative amount of the pest animal population; and thereafter
   (3) removing the trap and relating the number and/or type of animals arrested therein to the infestation status of the environment.

2. A method as claimed in claim 1 wherein the gel bait comprises between 65 and 98% weight water.

3. A method as claimed in claim 1 or wherein after the predetermined time the pest animals on the bait are enumerated, identified and/or further characterised.

4. A method as claimed in claim 1 wherein the trap includes an microbial detector capable of detecting the presence of one or more microorganisms associated with the insects and/or arachnid pest animals.

5. A method as claimed in claim 4 wherein the microbial detector comprises a microbial growth medium that undergos a colour change when microorganisms grow in or on it.

6. A method as claimed in claim 4 wherein the microbial growth medium is the aqueous gel body or further such body included in the trap.

7. A method as claimed in claim 1 wherein the pest animal is a mite.

8. A method as claimed in claim 1 wherein the predetermined time is from 1 to 10 days.

9. A method as claimed in claim 8 wherein the predetermined time is from 4 to 7 days.

10. A method as claimed in claims 1 wherein the environment is a stored produce or premises dealing with storage, production and/or distribution of produce.

11. A method according to claim 4 wherein the microbial detector comprises an absorbent body impregnated with antibodies.

12. A bait and trap for attracting and detaining insect and/or arachnid pest animals, comprising a housing having an adjustable opening to allow access of pest animals and mounting means on an interior surface of the housing for immobilizing a bait therein;

a bait non-harmful to the animal pests, comprising a non-flowing aqueous gel body formed from a mixture of an aqueous component and gel forming components, wherein the water content of the bait is sufficient to detain the insects within the housing when the adjustable opening is open sufficiently to allow access of the insect pest.

13. A bait and trap according to claim 12 wherein the housing comprises a lid portion and a base portion, said portions being movable relative to each other so as to produce the adjustable opening.

14. The bait and trap as claimed in claim 12 wherein the bait contains an agar, an alginate or both as gel-forming components.

15. The bait and trap as claimed in claim 12 wherein the water content of the gel body is from 65 to 98% by weight.

16. The bait and trap as claimed in claim 15 wherein the water content of the gel body is from 70 to 87% by weight.

17. The bait and trap as claimed in claim 12 wherein the bait or trap further includes a solid gel microbial detection medium body.

18. The bait and trap as claimed in claim 17 wherein the microbial detection medium body undergoes a color change when Salmonella and/or Listeria organisms grow on or in it.

19. The bait and trap as claimed in claim 17 wherein the microbial detection medium body is an absorbent body impregnated with antibodies to a target organism.

20. The bait and trap as claimed in claim 13 wherein the lid portion and a base portion are interconnectable by means of screw threads.

21. The bait and trap as claimed in claim 12 wherein the mounting means are such that a non-flowing solid gel bait can be releasable mounted thereon and removed without substantial damage to the bait occurring.

22. The bait and trap as claimed in claim 21 wherein the mounting means comprises one or more projections on or between which the bait is secured.

23. The bait and trap as claimed in claim 22 wherein the projections are suitable for mounting the bait by impaling the bait.

24. The bait and trap as claimed in claim 12 wherein a base of the trap is configured to allow stable placement upon a flat surface or wherein the trap has fixing means allowing its stable placement on angled or vertical surfaces.

25. The bait and trap as claimed in claim 24 wherein the fixing means comprises a cord on which the trap may be suspended.

* * * * *